United States Patent [19]

Phillipps et al.

[11] Patent Number: 4,933,457
[45] Date of Patent: Jun. 12, 1990

[54] PREPARATION OF 5,8,13,14-TETRAHYDROBENZ[5,6]ISOINDOLO[2,1-B]ISOQUINOLIN-8,13-DIONE DERIVATIVES

[75] Inventors: Gordon H. Phillipps, Wembley; Brian R. Cowley, Ruislip, both of United Kingdom

[73] Assignee: Glaxo Group Limited, London, England

[21] Appl. No.: 293,965

[22] Filed: Jan. 6, 1989

[30] Foreign Application Priority Data

Jan. 7, 1988 [GB] United Kingdom ............... 8800312

[51] Int. Cl.[5] ........................................ C07D 471/04
[52] U.S. Cl. ...................................... 546/23; 546/42
[58] Field of Search .................................. 546/42, 23

[56] References Cited

U.S. PATENT DOCUMENTS

| | | | |
|---|---|---|---|
| 3,336,317 | 8/1967 | Inman | 546/42 |
| 3,894,029 | 7/1975 | Winterfeldt et al. | 260/287 |
| 3,903,276 | 9/1975 | Nudelman et al. | 424/244 |
| 4,029,659 | 6/1977 | Hannart | 546/48 |
| 4,033,966 | 7/1977 | Sawa | 260/286 |
| 4,042,591 | 8/1977 | Kaul | 546/42 |
| 4,087,426 | 5/1978 | Shamma et al. | 260/286 |
| 4,301,285 | 11/1981 | Stein | 544/138 |
| 4,399,282 | 8/1983 | Miyasaka et al. | 546/48 |
| 4,434,290 | 2/1984 | Bisagni et al. | 546/70 |
| 4,444,776 | 4/1984 | Bisagni et al. | 424/258 |
| 4,548,819 | 10/1985 | DeClerq | 514/261 |
| 4,831,039 | 5/1989 | Dube et al. | 546/42 |
| 4,835,158 | 5/1989 | Phillipps et al. | 546/42 |
| 4,851,399 | 7/1989 | Phillipps et al. | 546/42 |

FOREIGN PATENT DOCUMENTS

| | | |
|---|---|---|
| 108620 | 5/1984 | European Pat. Off. . |
| 0161102 | 11/1985 | European Pat. Off. ............ 546/42 |
| 161102 | 11/1985 | European Pat. Off. . |
| 274842 | 7/1988 | European Pat. Off. . |
| 0274842 | 7/1988 | European Pat. Off. ............ 546/42 |
| 2129799 | 5/1954 | United Kingdom ................ 546/42 |
| 2175587 | 12/1986 | United Kingdom . |
| 2195636 | 4/1988 | United Kingdom . |
| 2210365 | 6/1989 | United Kingdom ................ 546/42 |

OTHER PUBLICATIONS

Heinzman et al., "Regiosp. Synth. Bromo Juglone Deriv.", Tetrahed. Lett., vol. 21, No. 45, pp. 4305–4308 (1980).
Thomson, "Chlorination of 1,5-Dihydroxynaphthalene", J. Org. Chem., vol. 13, pp. 371–376 (1948).
Thomson, "Stud. The Juglone Series", J. Org. Chem., vol. 13, pp. 377–383 (1948).
Chem. Abstracts (1971) 75:143961y (Affonso).
Chem. Abstracts (1972) 77:88260h (Dainis).
Chem. Abstracts (1975) 83:152267u (Kato).
Chem. Abstracts (1975) 83:168484y (Kasai).
Chem. Abstracts (1980) 92:75895d (Kishi).

Patent Abstracts of Japan, 8, 130, (C-229)[1567] 16-6-84 (Ikeda).
Uchida et al., J. Heterocyclic Chem., 15:1303–1307 (1978).
Fieser et al., Reagents for Organic Synthesis, Wiley, New York, 1967, 682–684.
Hershenson et al., J. Org. Chem., 37:3111–3113 (1972).
Spray, Ph.D. Thesis, University of Bath, England, 1980 (extracts).

Primary Examiner—Anton H. Sutto
Assistant Examiner—Andrew G. Rozycki
Attorney, Agent, or Firm—Bacon & Thomas

[57] ABSTRACT

A process is described for the preparation of compounds of formula (1)

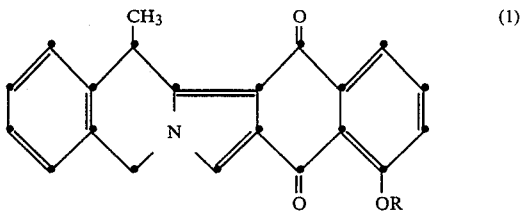

[where OR is hydroxyl, protected hydroxyl or OP(O)-(OCH$_2$Ph)(OR$^1$) (where Ph is phenyl and OR$^1$ is hydroxyl or protected hydroxyl)] and salts thereof, which comprises reacting a compound of formula (2)

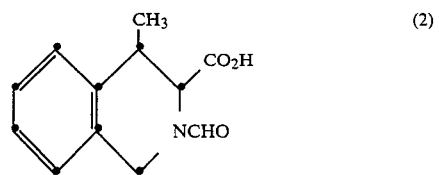

with a compound of formula (3)

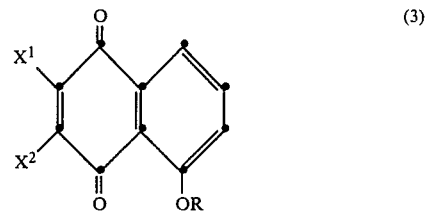

(where OR is as defined above and one of X$^1$ and X$^2$ is a leaving group and the other is a hydrogen atom) or a salt thereof, followed, if desired, by removal of the hydroxyl protecting group when present and/or by salt formation.

The compounds of formula (1) are either anticancer agents or intermediates useful in the synthesis of anticancer agents.

10 Claims, No Drawings

PREPARATION OF 5,8,13,14-TETRAHYDROBENZ[5,6]ISOINDOLO[2,1-B]ISOQUINOLIN-8,13-DIONE DERIVATIVES

This invention relates to a new process for the preparation of anticancer agents and for the preparation of intermediates used in the synthesis of anticancer agents. EP-A-161102 and GB-A-2195636 describe new isoquinoline derivatives having good anticancer activity and processes for their preparation. A key step in the synthesis of compounds described therein is the formation of an appropriately substituted 5,8,13,14-tetrahydrobenz[5,6]isoindolo[2,1-b]isoquinolin-8,13-dione ring system. Both EP-A-161102 and GB-A-2195636 describe the formation of such a ring system involving reacting an appropriate juglone derivative with a 1,2,3,4-tetrahydroisoquinoline 3-carboxylic acid. However, this reaction suffers from the disadvantage that two molar equivalents of the juglone derivative are required for every one molar equivalent of the 1,2,3,4-tetrahydroisoquinoline 3-carboxylic acid in order for the desired reaction to take place effectively. Furthermore, the products of EP-A-161102 and GB-A-2195636, including the more interesting 9-substituted products, are prepared therein starting from juglone itself (5-hydroxy-1,4-naphthalenedione) which is difficult to make and very expensive to buy.

We now describe herein a new process for the preparation of 9-substituted 5,8,13,14-tetrahydrobenz[5,6]isoindolo[2,1-b]isoquinolin-8,13-diones described in EP-A-161102 and GB-A-2195636. The present process is very convenient and may be used on an industrial scale. The process is also much more cost effective than the process described in the aforementioned published European and UK patent specifications and referred to above since it utilises cheaper and more readily available starting materials and the two components used in the process may conveniently be reacted in equimolar amounts. The present process can also proceed in a highly regiospecific manner and may be used to prepare the desired products in good yield.

Thus, according to one aspect of the present invention, we provide a process for the preparation of compounds of formula (1)

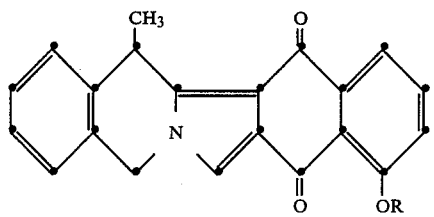

[wherein OR represents a hydroxyl group, a protected hydroxyl group or a group $OP(O)OCH_2Ph)(OR^1)$ (where Ph represents phenyl and $OR^1$ represents a hydroxyl group or a protected hydroxyl group)] and salts, e.g. physiologically acceptable salts, thereof, which process comprises reacting a compound of formula (2)

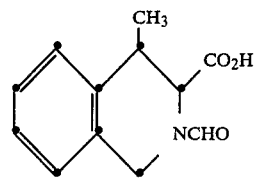

with a substituted 1,4-naphthoquinone of formula (3)

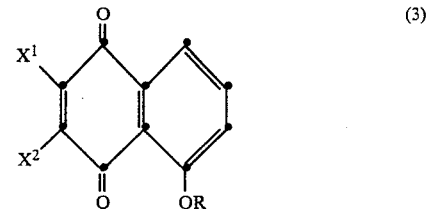

(wherein OR is as defined previously and one of $X^1$ and $X^2$ is a leaving group and the other is a hydrogen atom) or a salt thereof, and subsequently, if desired, removing any hydroxyl protecting group present, and subsequently, if desired, converting the compound of formula (1) thus obtained into a salt thereof.

The reaction between the compounds of formulae (2) and (3) is conveniently carried out in the presence of a dehydrating agent such as an alkanoic acid anhydride (e.g. acetic anhydride), preferably in the presence of a buffer such as a salt of a weak acid, for example a sodium carboxylate (e.g. acetate or sodium propionate) and at an elevated temperature (e.g. 50° to 100° C.).

The reaction may take place in the presence of a suitable aprotic solvent such as an ether (e.g. dioxan), a halogenated hydrocarbon (e.g. 1,1,1-trichloroethane) or a amide (e.g. N,N-dimethylformamide). However, when an alkanoic acid anhydride is used this is conveniently also the solvent for the reaction.

The term 'leaving group' in relation to formula (3) may denote any suitable displaceable atom or group, for example, a halogen atom such as chlorine or bromine or a hydroxyl, alkoxy (e.g. $C_{1-6}$ alkoxy such as methoxy), acyloxy (e.g. $C_{2-6}$alkanoyloxy such as acetoxy) or aryl- or alkane-sulphonyloxy (e.g. optionally substituted phenylsulphonyloxy such as tosyloxy or $C_{1-6}$alkanesulphonyloxy such as mesyloxy) group. However, preferably one of $X^1$ and $X^2$ is a halogen atom and the other is a hydrogen atom.

When OR or $OR^1$ represents a protected hydroxyl group the protecting group may be any conventional hydroxyl protecting group, for example as described in 'Protective Groups in Organic Chemistry' Ed. J. F. W. McOmie (Plenum Press 1973) or 'Protective Groups in Organic Synthesis' by Theodore W. Greene (John Wiley and Sons 1981). When OR represents a protected hydroxyl group this is conveniently an acyloxy (e.g. 2-6alkanoyloxy such as acetoxy or halomethylcarbonyloxy) group. When $OR^1$ represents a protected hydroxyl group this is conveniently a phenyl $C_{1-3}$ alkyl group such as a benzyloxy group.

In a particularly preferred embodiment of the process, $X^1$ represents a halogen atom (e.g. a bromine atom or, more preferably, a chlorine atom) and $X^2$ is a hydrogen atom. When $X^1$ represents a halogen atom and $X^2$ is a hydrogen atom the reaction proceeds in an extremely regiospecific manner to provide almost exclusively the desired 9-substituted compounds of formula (1). Many of the reactions described in EP-A-161102 generate both 9- and 12-substituted derivatives. Hence, the highly regiospecific nature of this aspect the present process represents an additional advantage over the process described in EP-A-161102 GB-A-2195636 and referred to above.

Where a mixture of 9- and 12- substituted derivatives are produced however following the process of the present invention, the desired 9-substituted compounds of formula (1) may be obtained by conventional separation techniques, such as chromatography using, for example, silica gel or by crystallisation.

The present process provides a particularly convenient method for preparing the compounds of formula (1) in which OR represents an acyloxy (e.g. acetoxy or halomethylcarbonyloxy) group. The corresponding compound of formula (I) in which OR represents a hydroxyl group is preferably prepared by deacylation of a compound of formula (1) in which OR represents acyloxy (e.g. acetoxy or halomethylcarbonyloxy) prepared from suitable compounds of formulae (2) and (3) according to the present process.

The compounds of formula (1) in which OR represents a hydroxyl group or an acyloxy group are key intermediate in the synthesis of the important anti-cancer agent phenylmethyl, [5,8,13,14-tetrahydro-14-methyl-8,13-dioxobenz[5,6]isoindolo[2,1-b]isoquinolin-9-yl]phosphoric acid (hereinafter referred to as 'Compound A'), a compound of formula (1) in which OR represents $OP(O)(OCH_2Ph)(OH)$, and physiologically acceptable salts thereof, especially the sodium salt.

Thus, according to a further aspect of the invention, we provide a multistep process for the preparation of Compound A and its physiologically acceptable salts which process comprises reacting a compound of formula (2) with a compound of formula (3) (wherein $X^1$ and $X^2$ are as defined previously and OR is a protected hydroxyl group, e.g. an acyloxy group such as acetoxy or halomethylcarbonyloxy) under the conditions described above to provide a compound of formula (1) in which OR is a protected hydroxyl group, followed by deprotection (e.g. deacylation), phosphorylation and deprotection, for example as described in "Route 1" hereinafter, to give the desired compound, Compound A or a physiologically acceptable salt thereof.

According to a further aspect of the invention we provide a multistep process for the preparation of Compound A and its physiologically acceptable salts which process comprises reacting a compound of formula (2) with a compound of formula (3) (wherein $X^1$ and $X^2$ are as defined previously and OR is a hydroxyl group) under the conditions described above to provide a compound of formula (1) in which OR is a hydroxyl group, followed by phosphorylation and deprotection, for example as described in "Route 2" hereinafter, to give the desired compound, Compound A or a physiologically acceptable salt thereof.

Compound A and its physiologically acceptable salts may also be prepared in two steps from a compound of formula (2) and a compound of formula (3) in which OR represents $OP(O)(OCH_2Ph)(OR^1)$ (wherein $X^1$ and $X^2$ are as defined previously and $OR^1$ represents a protected hydroxyl group). Thus, according to a yet further aspect of the present invention, we provide a process for the preparation of Compound A and its physiologically acceptable salts which process comprises reacting a compound of formula (2) with a compound of formula (3) in which OR represents $OP(O)(OCH_2Ph)(OR^1)$ (where $X^1$ and $X^2$ are as defined previously and $OR^1$ represents a protected hydroxyl group) under the conditions described above to provide a compound of formula (1) in which OR represents $OP(O)(OCH_2Ph)(OR^1)$ where $OR^1$ is a protected hydroxyl group followed by deprotection, for example as described in "Route 3" hereinafter, to provide the desired compound, Compound A or a physiologically acceptable salt thereof.

"Route 1" below [wherein in formulae (3) and (1a) the group OR is a protected hydroxyl group] provides a very convenient method of preparing Compound A and its physiologically acceptable salts. A particularly preferred of preparing Compound A and its physiologically acceptable salts involves "Route 1" below wherein the initial step (i) is carried out using a compound of formula (3) in which $X^1$ is a halogen atom, especially a chlorine atom, $X^2$ is a hydrogen atom and OR is an acyloxy group, especially acetoxy.

Route 1

(2) + (3) —(i)→ 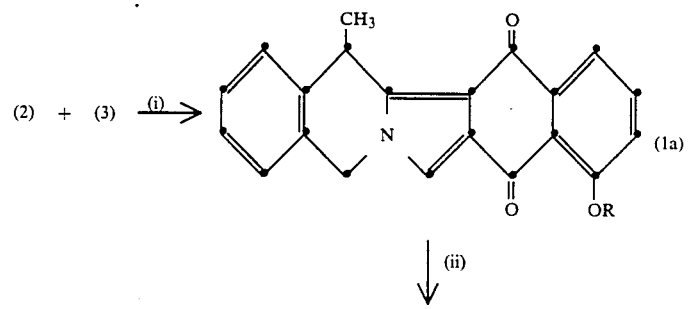 (1a)

↓ (ii)

-continued
Route 1

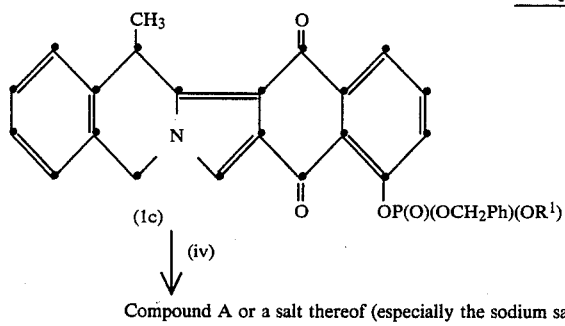
(1c)

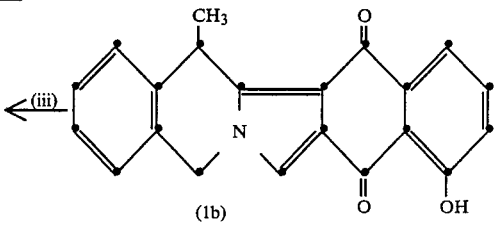
(1b)

↓ (iv)

Compound A or a salt thereof (especially the sodium salt)

Route 2

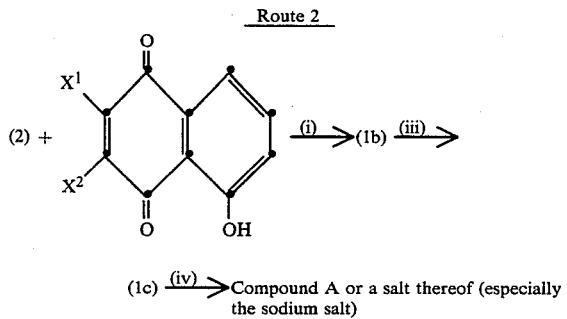

(1c) —(iv)→ Compound A or a salt thereof (especially the sodium salt)

Route 3

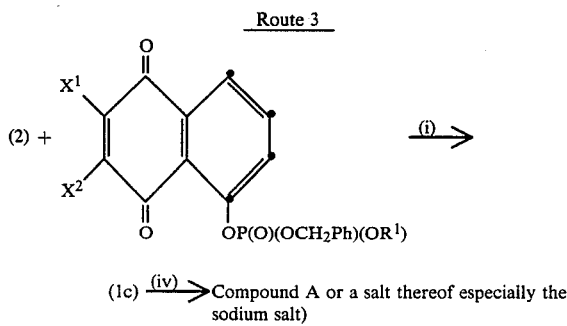

(1c) —(iv)→ Compound A or a salt thereof especially the sodium salt

Step (i) may be effected using the conditions described above for preparing compounds of formula (1) from compounds of formulae (2) and (3).

Step (ii) may be effected using standard methodology for removing hydroxy protecting groups. Thus, for example, when OR represents an acyloxy group such as acetoxy or halomethylcarbonyloxy deprotection to provide the 9-hydroxy compound of formula (1b) may be effected by hydrolysis using, for example, acid hydrolysis with an aqueous mineral acid (e.g. aqueous hydrochloride acid) or an organic acid (e.g. trifluoroacetic acid).

Steps (iii) and (iv) may be effected under the general conditions described in GB-A-2195636. Thus, Step (iii) may involve reacting a compound of formula (1b) with a halophosphate HalP(O)(OCH$_2$Ph)(OR$^1$) or a pyrophosphate (R$^1$O)(PhCH$_2$O)(O)P-O-P(O)(OCH$_2$Ph)(OR$^1$) (where OR$^1$ is as previously defined and is conveniently benzyloxy and Hal is a halogen atom e.g. chlorine) in the presence of a base, for example an alkali metal hydride such as sodium hydride, an alkali or alkaline earth metal carbonate e.g. potassium carbonate or an alkali or alkaline earth metal hydroxide e.g. potassium hydroxide, conveniently in an inert solvent such as an ether, e.g. tetrahydrofuran optionally also containing some water, an aromatic hydrocarbon e.g. toluene or a ketone e.g. acetone or a mixture of such solvents. The reaction may conveniently be carried out at a temperature in the range 0° to 100° C. e.g. 20° C. Step (iv) may be carried out by reacting the compound of formula (1c) with a nucleophile e.g. a halide ion such as an iodide ion (obtained, for example, from an alkali metal halide such as sodium iodide) or a quaternary ammonium halide such as triethylamine hydroiodide in an inert solvent such as a ketone (e.g. acetone or butan-2-one) optionally also containing some water, or a substituted amide (e.g. dimethylformamide). The reaction may be carried out at any suitable temperature, for example in the range −10° to +100° C. When an alkali metal halide (e.g. sodium iodide) is used the appropriate metal salt of Compound A (e.g. the sodium salt) is prepared.

Compound A may form salts with bases. Examples of salts of Compound A include alkali metal salts such as lithium, sodium or potassium salts, amine salts, for example ammonium and mon-, di- or tri-substituted ammonium e.g. triethylammonium salts and amino acid salts, for example arginine salts. Sodium salts are particularly useful. Where Compound A is produced in the acid form, a corresponding salt may be obtained by conventional means, e.g. by addition of a base providing the required cation, for example sodium hydroxide or an alkali metal carboxylate such as a sodium carboxylate (e.g. sodium 2-ethylhexanoate). Thus, a salt of Compound A may be prepared by treating Compound A with a suitable base in a solvent such as water, an ether e.g. tetrahydrofuran or an alcohol e.g. isopropyl alcohol or a mixture thereof. The reaction may conveniently be carried out at ambient temperature. Alternatively, a salt of Compound A may be obtained by treating a suitable compound of formula (1c) with an alkali metal halide (e.g. lithium iodide, sodium iodide or potassium iodide) in a suitable solvent such as water or a ketone (e.g. acetone or butan-2-one) or a mixture thereof, conveniently at ambient temperature. An amino acid salt of Compound A may be obtained by treating Compound A with an amino acid, e.g. L-arginine monohydrate in water at ambient temperature. A salt of Compound A may be converted to a different salt, e.g. a physiologically acceptable salt, by exchange of ion using conventional means.

The compound of formula (2) is a known compound described in EP-A-161102. The compounds of formula (3) are either known compounds described by S. W. Heinzmann and J. R. Grunwell in Tetrahedron Letters, 1980, 21 (45), 4305-8 or by R. H. Thomson in J. Org.

Chem, 1948, 13, 371–383 or may be prepared from known compounds using methods analogous to those described therein.

The following non-limiting Examples illustrate the invention. All temperatures are in °C. Unless otherwise stated all UV spectral data relate to solutions in methanol of the compounds concerned and all ratios are by volume.

INTERMEDIATE 1

Bis(phenylmethyl), [2-chloro-1,4-dioxonaphth-5-yl]phosphate

A stirred solution of 2-chloro-5-hydroxy-1,4-naphthoquinone (834 mg) in acetone (70 ml) was treated under nitrogen with dibenzyl chlorophosphate (2.25 g) and potassium carbonate (3.51 g). The mixture was stirred vigorously and heated to 50° over 15 min and then kept at 50°–55° for a further 45 min. The cooled mixture was filtered and the filtrate was evaporated to a brown oil. This oil was chromatographed on silica gel (ca. 50 g), eluting with dichloromethane-acetone (96:4), to give a yellow-orange solid. This solid was purified by repeated trituration with diisopropyl ether to give the title compound (1.02 g), $\lambda_{max}$ 268 nm, $E_1^1$ 306; $\delta$(CDCl$_3$) 8.02 (8-H,d,6 Hz,1H), 5.31 and 5.21 C$_6$H$_5$CH$_2$,q,11 Hz,d,8 Hz, $^3$JP,4H).

INTERMEDIATE 2

2-Bromo-5-[iodoacetoxy]-1,4-naphthoquinone

A solution of 2-bromo-5-hydroxyl-1,4-naphthoquinone (3.6 g) in acetone (36 ml) was cooled to 5° and chloroacetyl chloride (1.69 ml) was added. Triethylamine (2.96 ml) was added over 15 min keeping the temperature at 5°, and the mixture was stirred for 30 min. The reaction was completed by addition of more chloroacetyl chloride (0.34 ml) and then a further portion of triethylamine (0.6 ml) over 5 min. The mixture was stirred for 10 min and then poured into water (360 ml). The precipitate was collected by filtration, washed with water (2×25 ml), sucked dry for 2 h and then redissolved in acetone (37 ml). Sodium iodide (2.1 g) was added and the solution was stirred under nitrogen for 16 h at 20° and then poured into water (300 ml). This mixture was aged for 30 min and the fine precipitate was collected by filtration, washed with water (10 ml) and dried in vacuo at 40° to give the title compound as a brown solid (1.0 g), $\delta$ (CDCl$_3$) 8.18 (8-H,dd,9 and 2 Hz, 1H), 7.81 (7-H,t,10 Hz,1H), 7.48 (6-H,dd,10 and 2 Hz,1H), 7.39(3-H,s,1H), 4.10(COCH$_2$I,s2H).

EXAMPLE 1

Bis(phenylmethyl),[5,8,13,14-tetrahydro-14-methyl-8,13-dioxobenz[5,6]isoindolo[2,1-b]isoquinolin-9-yl]phosphate A mixture of Intermediate 1 (469 ml), N-formyl-1,2,3,4-tetrahydroisoquinoline-4-methyl-3-carboxylic acid monohydrate (237 mg), anhydrous sodium acetate (82 mg) and acetic anhydride (2 ml) was stirred under nitrogen and heated at 70°–80° for 45 min and then at 80°–82° for a further 4.5 h. The cooled mixture was evaporated in vacuo and the residue was triturated with water (25 ml). The resulting gum was dissolved in dichloromethane (10 ml). The aqueous phase was extracted with more dichloromethane (10 ml) and the combined organic extract was washed with water (2×10 ml) and evaporated in vacuo. The residual viscous gum was dissolved in dichloromethane (1.5 ml) and the solution was diluted slowly with diisopropyl ether (6 ml). Separation of some of the resulting yellow crystals by filtration followed by washing with diisopropyl ether (2×3 ml) and drying in vacuo gave the title compound (93 mg), $\lambda_{max}$ 244 nm, $E_1^1$ 739, having a similar N.M.R. spectrum (CDCl$_3$) to an authentic sample prepared as Intermediate 5a in GB-A-2195636.

EXAMPLE 2

5,8,13,14-Tetrahydro-9-hydroxy-14-methylbenz[5,-6]isoindolo[2,1-b]-isoquinoline-8,13-dione A mixture of 2-chloro-5-hydroxy-1,4-naphthoquinone (1.043 g), N-formyl-1,2,3,4-tetrahydroisoquinoline-4-methyl-3-carboxylic acid monohydrate (1.186 g), anhydrous sodium acetate (410 mg) and acetic anhydride (9 ml) was heated at 80°–85° for 1.5 h. The resulting suspension was cooled to 21° and the solid was filtered off, washed with acetic anhydride (1.2 ml), ethyl acetate (1.2 ml), diisopropyl ethe (2×1.4 ml) and water (3×5 ml) and dried in vacuo to give a lemon solid. r Part (1.00 g) of this solid was added to a mixture of tetrahydrofuran (22 ml), concentrated hydrochloric acid (2.8 ml) and water (5.2 ml) and the resulting suspension was heated to reflux under nitrogen for 20 h and then cooled to 20°. The solid was filtered off, washed with tetrahydrofuran-water (2:1, 2×10 ml) and water (2×10 ml), and dried in vacuo at 35° to give the title compound (0.60 g), having a similar N.M.R. spectrum (CDCl$_3$) to an authentic sample prepared as Intermediate 3 in GB-A-2195636.

EXAMPLE 3

5,8,13,14-Tetrahydro-9-acetoxy-14-methylbenz[5,-6]isoindolo[2,1-b]isoquinoline-8,13-dione A mixture of 5-acetoxy-3-bromo-1,4-naphthoquinone (250 mg), 1,2,3,4-tetrahydroisoquinoline-4-methyl-3-carboxylic acid monohydrate (201 mg), anhydrous sodium acetate (70 mg) and acetate anhydride (1.5 ml) was stirred under nitrogen and heated at 70°–80° for 4.25 h. Part of the solvent was removed in vacuo and the residue was suspended in water (20 ml) and left overnight. The solid was filtered off, washed with water (2×5 ml) and dried in vacuo at 30° to give a solid (283 mg) shown to contain the title compound by comparison with the N.M.R. spectrum (CDCl$_3$) of the sample obtained in Example 5 below.

EXAMPLE 4

5,8,13,14-Tetrahydro-9-hydroxy-14-methylbenz[5,-6]isoindolo[2,1-b]isoquinoline-8,13-dione A mixture of 2-bromo-5-hydroxy-1,4-naphthoquinone (1.265 g), N-formyl-1,2,3,4-tetrahydroisoquinoline-4-methyl-3-carboxylic acid monohydrate (1.186 g), anhydrous sodium acetate (0.41 g) and acetic anhydride (9 ml) was stirred under nitrogen and heated at 85°–90° for 1 h and 90°–73° for a further hour. The resulting suspension was cooled to 20° and the solid was filtered off, washed with acetic anhydride (1.2 ml), ethyl acetate (1.2 ml) and diisopropyl ether (2×1.2 ml), sucked dry and resuspended in water (5 ml). The suspension was filtered and the filter cake was washed with water (3×5 ml). The resulting lemon solid was dried in vacuo to give a solid (0.32 g) shown to contain the title compound by comparison with the N.M.R. spectrum (CDCl$_3$) of an authentic sample prepared as Intermediate 3 in GB-A-2195636.

EXAMPLE 5

5,8,13,14-Tetrahydro-9-acetoxy-14-methylbenz[5,6]isoindolo[2,1-b]-isoquinoline-8,13-dione A mixture of N-formyl-1,2,3,4-tetrahydroisoquinoline-4-methyl-3-carboxylic acid (18.57 g), 5-acetoxy-2-bromo-1,4-naphthoquinone (25.0 g), sodium acetate (6.875 g) and acetic anhydride (75 ml) was stirred under nitrogen and heated at 60° when all the solid had dissolved. The sources of heat was removed and the temperature was allowed to rise to 85° and then fall back to 60° over 30 min. The reaction was completed by heating the mixture at 70°–80° for 30 min and then cooled to 20° and stirred for 30 min. The precipitate was collected by filtration, washed successively with acetic anhydride (2×25 ml), ethyl acetate (12.5 ml) and diisopropyl ether (2×12.5 ml) and dried in vacuo at 40°. The resulting solid was stirred with water (300 ml) for 30 min and then collected by filtration, washed with water (50 ml) and dried in vacuo at 40° to give the title compound (27.3 g), $\lambda_{max}$ 243 mn, $E_1^1$ 794; $\delta$(CDCl$_3$) 5.22 (5-H,d 16 Hz,1H), 5.12 (5-H,d,16 Hz, 1H), 4.93(14-H,q,7 Hz,1H), 2.48 (OCOCH$_3$,s,3H), 1.53(14-CH$_3$,d,7 Hz,3H).

EXAMPLE 6

5,8,13,14-Tetrahydro-9-acetoxy-14-methylbenz[5,6]iosoindolo[2,1-b]-isoquinoline-8,13-dione A mixture of N-formyl-1,2,3,4-tetrahydroisoquinoline-4-methyl-3-carboxylic acid (21.8 g), 5-acetoxy-2-chloro-1,4-naphthoquinone (25.0 g), sodium acetate (8.2 g) and acetic anhydride (88 ml) was stirred under nitrogen and heated to 60°. The source of heat was removed and the temperature was allowed to rise to 105° and then fall back to 70° over 30 min. The reaction was completed by heating the mixture at 70°–80° and then cooled to 20° and stirred for 30 min. The precipitate was collected by filtration, washed with acetic anhydride (2×6.25 ml), ethyl acetate (12.5 ml) and diisopropyl ether (12.5 ml) and dried in vacuo at 40°. The resulting solid was stirred with water (350 ml) for 30 min and then collected by filtration, washed with water (50 ml) and dried in vacuo at 40° to give the title compound (30.34 g), $\lambda_{max}$ 243 nm, $E_1^1$ 679, having a similar N.M.R. spectrum (CDCl$_3$) to the sample obtained in Example 5 above.

EXAMPLE 7

5,8,13,14-Tetrahydro-9-[iodoacetoxy]-14-methylbenz[5,6]isoindolo-[2,1-b]isoquinoline-8,13-dione A mixture of N-formyl-1,2,3,4-tetrahydroisoquinoline-4-methyl-3-carboxylic acid (220 mg), Intermediate 2 (421 mg), sodium acetate (80 mg) and acetic anhydride (2 ml) was heated on a steam bath for 1 h. The solvent was removed by evaporation under reduced pressure, the residue was dissolved in dichloromethane (25 ml) and the resulting solution was washed with 8% aqueous sodium hydrogen carbonate solution (25 ml), dried over anhydrous magnesium sulphate and evaporated to give the title compound (420 mg), $\delta$(CDCl$_3$) 8.18 (12-H,dd,8 and 2 Hz,1H), 7.64 (11-H,t,9 Hz,1H), 5.16(5-H,d,16 Hz,1H), 5.06(5-H,d,16 Hz,1H), 4.87(14-H,q,7 Hz,1H), 4.08 (COCH$_2$I,s,2H), 1.46(CH$_3$,d,7 Hz,3H).

EXAMPLE 8

Phenylmethyl,[5,8,13,14-tetrahydro-14-methyl-8,13-dioxobenz[5,6]-isoindolo[2,1-b]isoquinolin-9-yl]phosphoric acid, sodium salt (a)

5,8,13,14-Tetrahydro-9-hydroxy-14-methylbenz[5,6]isoindolo[2,1-b]-isoquinoline-8,13-dione (i) A suspension of the product of Example 6 above (62.11 g) in a mixture of tetrahydrofuran (890 ml), concentrated hydrochloric acid (137 ml) and water (201 ml) was stirred and heated under reflux under nitrogen for 17 h, and part (400 ml) of the solvent was removed by distillation at atmospheric pressure. The resulting suspension was stirred and cooled to ca. 5° for 2 h, and the solid was collected by filtration, washed with tetrahydrofuran-water (2:1, 2×150 ml) and dried in vacuo at 40° for 3 h and then at 21° for 48 h to give the title compound (47.95 g), having a similar N.M.R. spectrum (CDCl$_3$) to an authentic sample prepared as Intermediate 3 in GB-A-2195636.

(ii) Water (312 ml) and concentrated hydrochloric acid (169 ml) were added to a suspension of the product of Example 7 above (80.0 g) in tetrahydrofuran (1.335 L). This mixture was stirred and heated to reflux under nitrogen for 18 h and part (550 ml) of the solvent was removed by distillation at atmospheric pressure. The resulting suspension was stirred and cooled to ca. 5° for 4.5 h, and the solid was collected by filtration, washed with cold tetrahydrofuran and dried in vacuo to give the title compound (48.8 g), $\lambda_{max}$ 243 nm, $E_1^1$ 1022; $\delta$ (CDCl$_3$) 12.98 (OH,s,1H), 5.27 (5-H,d,16 Hz,1H), 5.16 (5-H,d,16 Hz,1H), 4.98 (14-H,q,7 Hz,1H), 1.55 (14-CH$_3$,d,7 Hz,3H).

(b)

Bis(phenylmethyl,[5,8,13,14-tetrahydro-14-methyl-8,13-dioxobenz[5,6]isoindolo[2,1-b]isoquinolin-9-yl]phosphate (i) N-chlorosuccinimide (1.017 g) was added to a stirred solution of dibenzyl phosphite (3.3 ml) in dry benzene (30 ml) and the resulting solution was stirred at 20°, the succinimide was removed by filtration and the filtrate was concentrated to a low volume (about 5–10 ml). This solution was then used as follows:

A 60%-dispersion of sodium hydride in oil (134 mg) was washed free of oil with 40°–60° petroleum spirit (2×15 ml) under a nitrogen atmosphere. Dry tetrahydrofuran (25 ml) was added to the sodium hydride followed by addition of the product of Example 8a above (1.0 g) in dry tetrahydrofuran (100 ml). The resulting red solution was cooled to 10° in an ice-bath and treated with freshly prepared dibenzyl chlorophosphate in benzene (about 5–10 ml), see above). After 2 h at 10°, the reaction mixture was allowed to warm to 20° and maintained at this temperature for 3 h. The reaction mixture was diluted with water (500 ml) and extracted with dichloromethane (3×250 ml). The combined organic extracts were dried over anhydrous sodium sulphate and evaporated to a green oil which was dissolved in dichloromethane and applied to a column of silica (300 g) prepared using dichloromethane-acetone (96:4). The column was eluted with dichloromethane-acetone (96:4) and 25 ml fractions were collected. The product containing fractions were combined and evaporated to yield the title compound as a green foam (1.211 g), $\lambda_{max}$ (ethanol) 244 nm, $E_1^1$ 743, 374 nm, $E_1^1$ 112; $\delta$ (CDCl$_3$)

5.20–5.40 (OCH₂C₆H₅,m,4H), 5.23 (5-H,d,16 Hz,1H), 5.13 (5-H,d,16 Hz,1H), 4.95 (14-H,q,7 Hz,1H), 1.55 (14-CH₃,d,7 Hz,3H).

(ii) A solution of sulphuryl chloride (10.06 ml) in toluene (28 ml) was added to stirred dibenzyl phosphite (29.5 ml) in toluene (110 ml) under nitrogen over 25 min, while maintaining the reaction temperature between 6° and 13°. After the addition was complete, nitrogen was bubbled into the reaction mixture for 85 min which was then washed with 8% w/v aqueous sodium bicarbonate solution (200 ml). The separated organic layer was dried over anhydrous magnesium sulphate and concentrated in vacuo (bath temperature ca 40°) to an oil (37.7 g). which was diluted with toluene (37.7 ml) and used as follows:

To a solution of 85% potassium hydroxide (1.33 g) in tetrahydrofuran (40 ml; passed through basic aluminum) and distilled water (2.64 ml) was added the product of Example 8a above (4 g) and the mixture was stirred for 30 min. Freshly prepared dibenzyl chlorophosphate solution (14.04 g, see above) was added over 10 min. The reaction mixture was stirred for a further 1 h at ca 20°, diluted with distilled water (160 ml) and extracted with dichloromethane (2×25 ml). The organic extract was washed with distilled water (2×25 ml) and then evaporated to an oil. This oil was crystallised from dichloromethane (12 ml) and di-isopropyl ether (48 ml) to give the title compound as a green crystalline solid (6.4 g) having a similar N.M.R. spectrum (CDCl₃) to the sample obtained in Example 8(b)(i) above.

(c)
Phenylmethyl,[5,8,13,14-tetrahydro-14-methyl-8,13-dioxobenz[5,6]isoindolo[2,1-b]isoquinolin-9-yl]phosphoric acid, sodium salt (i) Sodium iodide (1.551 g) was added to a solution of the product of Example 8(b)(i) above (5.546 g) in acetone (100 ml) and the resulting solution was heated under reflux for 1.5 h. The reaction mixture was evaporated to dryness and the residue was tritureted with ether (100 ml) to give a yellow solid. This solid was dissolved in water (200 ml) and the pH of the solution was adjusted to pH 1 to 2 by the addition of 2M-hydrochloric acid. The resulting mixture was diluted with water (200 ml) and extracted with dichloromethane (2×400 ml). Salt solution was added during the extraction procedure to disperse the emulsion which was formed. The combined organic extracts were dried over anhydrous sodium sulphate and evaporated to a green solid. This solid was suspended in water (300 ml) and the suspension was adjusted to pH 7.0 by the dropwise addition of 1M-sodium hydroxide solution. The resulting solution was filtered and the filtrate was freeze-dried to a solid which was treated with acetone (400 ml) and evaporated to dryness to give a solid. Trituration of this solid with ether (200 ml) gave the title compound as a yellow solid (4.23 g), λ_max(ethanol) 244 nm, E₁¹ 679, 367 nm, E₁¹ 132; δ(d₆-DMSO) 5.41 (5-H,d,16 Hz,1H), 5.31 (5-H,d,16 Hz,1H), 4.93 (OCH₂C₆H₅,d,6 Hz,2H), 4.82 (14-H,q,7 Hz,1H), 1.47 (14-CH₃,d,7 Hz,3H).

(ii) Sodium iodide (1.39 g) was added to a solution of the product of Example 8(b)(ii) above (5 g) in acetone (100 ml) and the resulting solution was refluxed for 95 min. The reaction mixture was cooled to 30° and filtered. The filtered solution was stirred and warmed to 50°–57° and treated with a solution of distilled water (2.5 ml) and acetone (2.5 ml). The reaction mixture was stirred at ca. 55° for 20 min, cooled to 20° over 45 min and then stirred at this temperature for 1.5 h. The product was collected by filtration, washed with acetone (2×15 ml) and dried in vacuo at 30° to give the title compound as a crystalline yellow solid (4.22 g), having a similar N.M.R. spectrum (DMSO-d⁶) to the sample obtained in Example 8(c)(i) above.

We claim:

1. A process for the preparation of compounds of formula (1)

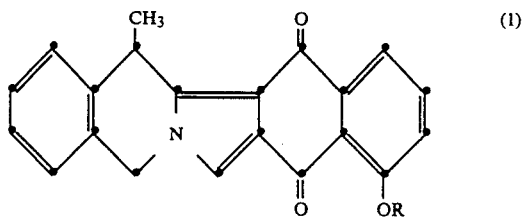

wherein OR represents a hydroxyl group, a protected hydroxyl group or a group OP(O)(OCH₂Ph)(OR¹) (where Ph represents phenyl and OR¹ represents a hydroxyl group or a protected hydroxyl group) and salts thereof, which process comprises reacting a compound of formula (2)

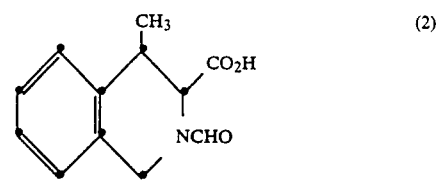

with a compound of formula (3)

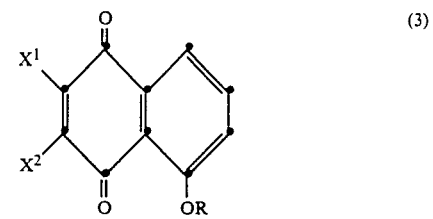

(wherein OR is as defined above and one of X¹ and X² is a leaving group and the other is a hydrogen atom) or a salt thereof, and subsequently, if desired, removing any hydroxyl protecting group present, and subsequently, if desired, converting the compound of formula (1) thus obtained into a salt thereof.

2. A process as claimed in claim 1 wherein as said compound of formula (3) is used a compound wherein OR represents an acyloxy group.

3. A process as claimed in claim 1 wherein as said compound of formula (3) is used a compound wherein OR represents an acyloxy group and wherein the compound of formula (1) thus obtained is deacylated whereby to yield a compound of formula (1) wherein OR represents a hydroxyl group.

4. A process as claimed in claim 1 wherein as said compound of formula (3) is used a compound wherein one of X¹ and X² is a halogen atom and the other is a hydrogen atom.

5. A process as claimed in claim 1 wherein as said compound of formula (3) is used a compound wherein $X^1$ represents a halogen atom and $X^2$ represents a hydrogen atom.

6. A process as claimed in claim 1 wherein the reaction between compounds of formulae (2) and (3) is effected in the presence of an alkanoic acid anhydride, in the presence of a buffer and at elevated temperature.

7. A process as claimed in claim 6 wherein said buffer is sodium acetate.

8. A process as claimed in claim 6 wherein the reaction between compounds of formulae (2) and (3) is effected at a temperature in the range of 50° C. to 100° C.

9. A process as claimed in claim 1 wherein the compound of formula (1) produced is subsequently separated from any side products.

10. A process as claimed in claim 7 wherein the reaction between compounds of formulae (2) and (3) is effected at a temperature in the range of 50° C. to 100° C.

* * * * *